United States Patent [19]
Pirmantgen et al.

[11] Patent Number: 4,565,190
[45] Date of Patent: Jan. 21, 1986

[54] KNEE ORTHOSIS WITH SWIVEL-ACTION SUPRACONDULAR CUFF

[75] Inventors: Robert E. Pirmantgen; John S. Adamski; Mark F. Devens, all of Chicago, Ill.

[73] Assignee: Northwestern University, Evanston, Ill.

[21] Appl. No.: 630,649

[22] Filed: Jul. 13, 1984

[51] Int. Cl.$^4$ ............................................. A61F 3/00
[52] U.S. Cl. .................................... 128/80 C; 128/88
[58] Field of Search ................ 128/80 R, 80 C, 80 F, 128/88, 80 G, 68, 77

[56] References Cited

U.S. PATENT DOCUMENTS

| | | | |
|---|---|---|---|
| 575,199 | 1/1897 | Autenrieth | 128/88 |
| 1,336,695 | 4/1920 | Gromes | 128/88 |
| 3,235,258 | 2/1966 | Stroburg | 128/88 X |
| 4,361,142 | 11/1982 | Lewis et al. | 128/80 C |
| 4,487,200 | 12/1984 | Feanny et al. | 128/80 C |

Primary Examiner—Clifford D. Crowder
Attorney, Agent, or Firm—Tilton, Fallon, Lungmus

[57] ABSTRACT

A knee orthosis for the protective treatment of ligamentous injuries or deficiencies, or as a supplement to total joint replacement, in which pairs of hinged sidebars are located on opposite sides of a wearer's leg, the orthosis including a system of suspension cuffs that engage the leg above and below the knee to maintain the medial and lateral orthotic joints in proper positions to restrain abnormal knee movements or, in the case of prosthetic joint replacement, prevent movements that do not conform with the prescribed action of the replaced joint. Two such cuffs engage the upper leg, the more distal of the two taking the form of a supracondular cuff adapted to extend about the leg just above the knee and including a semi-rigid medial member of developed shape mounted for limited swivel action.

11 Claims, 9 Drawing Figures

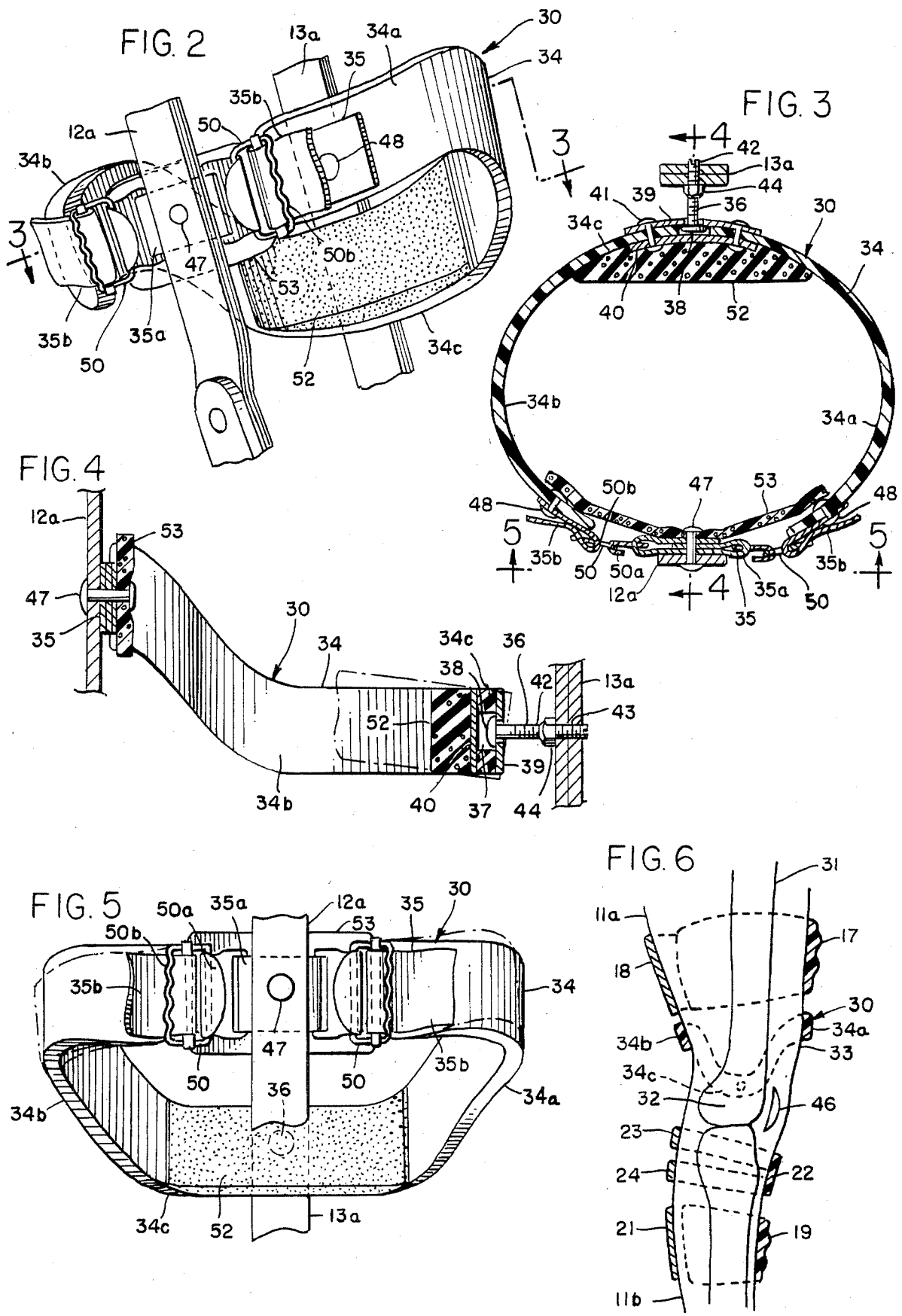

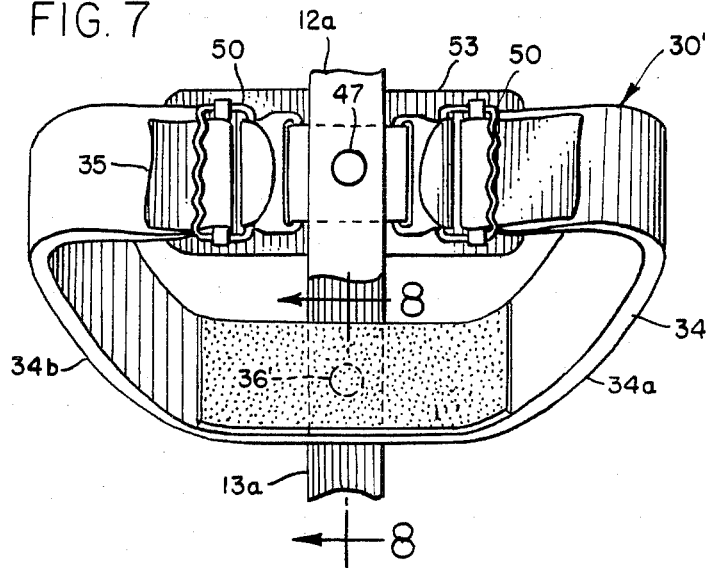
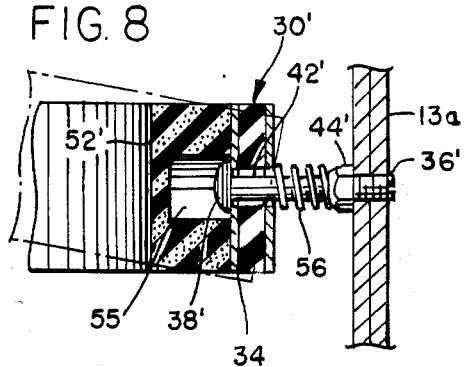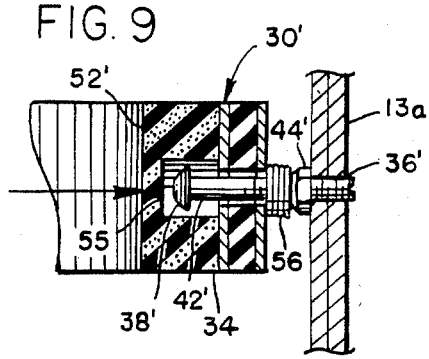

KNEE ORTHOSIS WITH SWIVEL-ACTION SUPRACONDULAR CUFF

BACKGROUND

U.S. Pat. No. 4,361,142 discloses a knee orthosis having a pair of knee joint assemblies 13 and 14 positioned on opposite sides of a patient's knee, each assembly having sidebars 15 and 16 extending alongside the upper leg and lower leg, respectively. The upper sidebars are in part held along the upper leg by a proximal femoral cuff consisting of a rigid or semi-rigid proximal interfacial member or plate 17 that is shaped to conform to the front (anterior) contour of the upper leg and is rigidly connected to the upper sidebars 15. A suspension strap 20 extends behind the leg and is adjustably connected to plate 17 (using Velcro patches or other ajustable connecting means) to form the proximal cuff about the wearer's thigh.

A second suspension strap 21 extends between upper sidebars 15 below the proximal cuff and, as shown in Figure 1 of the patent, extends only about the rear (posterior) portion of the upper leg. The purpose of strap 21 and pad 26 is to complement the suspending action of the proximal cuff and, in particular, hold the upper sidebars in proper positions against the sides of the wearer's leg. Two additional points or areas of suspension are located below (distal to) the knee, one being provided by a distal tibial cuff composed of interfacial element 18 and strap 20, and the other by a more proximal tibial cuff consisting essentially of interfacial member 19 and straps 23, 24.

As indicated in the patent, the purpose of the suspension cuffs is to immobilize the upper and lower sidebars 15 and 16 in relation to the leg in order to maintain the lateral and medial joints of the orthosis in position along opposite sides of the wearer's knee. While the orthotic joints described in the patent have been found effective in achieving the desired results if the sidebars 15 and 16 are sufficiently immobilized with respect to the upper and lower leg, some difficulties have been encountered in achieving such immobilization and avoiding "pistoning" or longitudinal shifting of the orthosis as the patient moves about. The problems occur more notable with physically active patients having strong muscular development of the legs but, in view of the fact that the orthosis is particularly suited for treating athletic injuries, a substantial proportion of the patients may be so characterized.

SUMMARY OF THE INVENTION

While U.S. Pat. No. 4,361,142 describes three areas of suspension, the lower femoral strap 21 and pad 26 might properly be regarded as a fourth area or zone of suspension. The effectiveness of that fourth suspension zone would be enhanced if the strap 21 extended completely about the upper leg since such extension would help to prevent sagittal pivotal action of sidebars 15 about their upper ends. However, it has now been discovered that such extension of strap 21 generally will still fall short of achieving acceptable immobilization of sidebars 15 because of substantial changes in the shape and location of the muscle mass directly above and medial to the knee when the leg is flexed and extended. Such changes in the muscle mass, particularly in the muscles of the quadricep group, exert forces upon the orthosis that may result in a longitudinal pistoning action and an ultimate downward displacement of the orthosis along the wearer's leg, thereby shifting the joints of the orthosis out of proper alignment with the knee joint of the wearer. Such downward displacement is found to be reduced if the strap of the fourth suspension zone is highly flexible, and especially if it is formed of elastic material; however, in that event the construction has been found lacking in its capability for preventing pivotal action of the upper sidebars 15 and undesirable anterior-posterior movement of their lower ends and of the orthotic joints to which they are connected.

One aspect of this invention therefore lies in so discovering the causes of pistoning and both anterior-posterior and longitudinal displacement of such a knee orthosis. A further aspect lies in the discovery that such problems may be avoided or greatly reduced if a supracondular cuff, having an arcuate semi-rigid support member, is mounted upon one of the upper sidebars of the orthosis so that the semi-rigid member is capable of limited swivel action. Such swivel action permits the cuff to accommodate or adjust to changes in muscle masses (particularly of the quadricep group) as the leg is flexed and extended. Since the support member is semi-rigid, it restrains pivotal action of the sidebars about their upper ends, thereby preventing anterior/posterior movement of the orthotic joints during flexion and extension. The result is an orthosis with an improved suspension system which more effectively maintains the orthotic joints in alignment with the knee joint and eliminates or greatly reduces pistoning regardless of changes in the location and shape of muscle masses as the leg is flexed and extended.

Briefly, the orthosis includes a pair of hinge assemblies intended to be located on opposite sides (medial and lateral) of a wearer's knee, each assembly including an upper sidebar that extends upwardly alongside the wearer's upper leg and a lower sidebar extending downwardly alongside the lower leg. The hinge itself is preferably the same as disclosed in the aforementioned patent; specifically, each hinge is designed so that it has constantly changing instantaneous axes of rotation as the upper and lower sidebars are moved between extension and flexion.

The suspension system includes lower suspension elements for holding the lower sidebars against the lower leg and upper suspension elements for supporting the upper sidebars against the upper leg. The suspension system may be generally regarded as a four-point suspension with distinctiveness particularly relating to the two-point (or two-zone) suspension arrangement above the knee.

Specifically, the upper suspension includes (a) a proximal cuff connected to the upper or proximal ends of the upper sidebars and designed to extend about the wearer's thigh and (b) a supracondular femoral cuff also connected to the upper sidebars but located distal to the proximal cuff. The supracondular femoral cuff includes a semi-rigid but flexible member of generally U-shaped configuration (when viewed in plan) having posterior and anterior arm portions arching upwardly and outwardly (laterally) from an integral intermediate portion. The intermediate portion of the semi-rigid interfacial member is connected to one of the upper sidebars (the medial sidebar) in a way that permits limited universal swivel or pivotal action. Flexible but substantially nonelastic straps join ends of the arm portions to the other of the upper sidebars (the lateral sidebar) with the interconnections between the strap and that sidebar being pivotal (in a sagittal plane) and with the straps being adjustably and detachably connected to the arm portions of the semi-rigid U-shaped member.

The pivotal connection between the U-shaped member and the medial upper side bar takes the form of a pivot pin secured at its inner (medial) end to the sidebar and at its outer (lateral) end to the U-shaped member. The shank of the pin may extend through an enlarged opening in the member and terminate in an enlarged head that serves to retain the member without restraining pivotal movement in sagittal, longitudinally transverse, and cross-sectionally transverse planes. The shank of the pin is threaded and is adjustably received in a threaded opening formed in the medial sidebar. A locking nut secures the pin in a selected axial position of adjustment and, in one form of the invention, a compression spring is interposed between the medial sidebar and the U-shaped member to permit limited transverse movement of the supracondular cuff and to exert a spring force urging that cuff laterally.

Other features, advantages, and objects of the invention will become apparent from the specification and drawings.

DRAWINGS

FIG. 2 is a fragmentary perspective view of the supracondular cuff for the orthosis.

FIG. 3 is a generally horizontal transverse sectional view taken along line 3—3 of FIG. 2.

FIG. 4 is a longitudinal transverse sectional view taken along line 4—4 of FIG. 3.

FIG. 5 is a fragmentary side elevational view taken along line 5—5 of FIG. 4.

FIG. 6 is a somewhat schematic sagittal view of the leg illustrating the supracondular femoral cuff in relation to other elements of the suspension system.

FIG. 7 is a fragmentary side elevational view showing a knee orthosis with a modified supracondular cuff.

FIG. 8 is a sectional view taken along line 8—8 of FIG. 7.

FIG. 9 is a sectional view similar to FIG. 8 but illustrating the spring in a compressed state.

DETAILED DESCRIPTION

Figure 1:
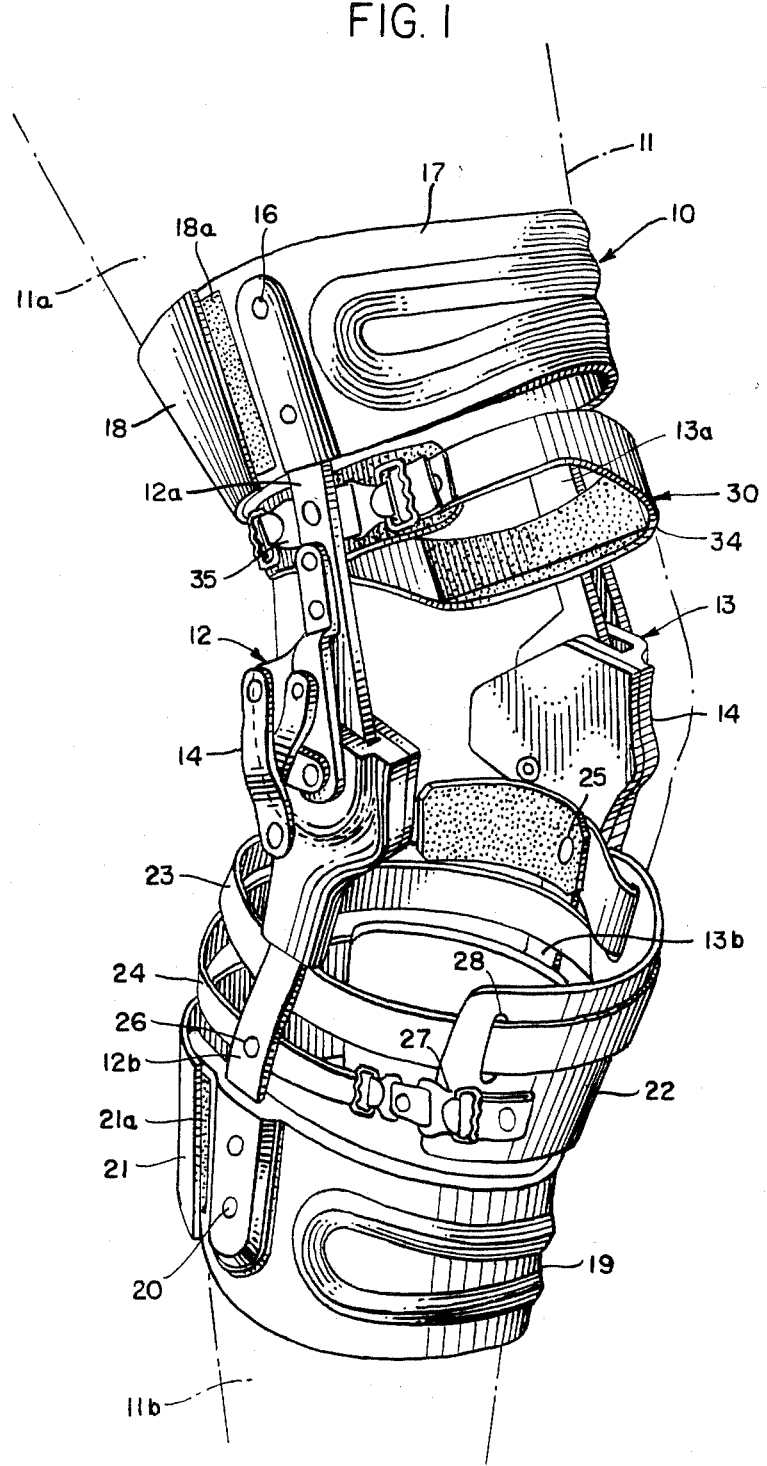
FIG. 1 is a perspective view of a knee orthosis embodying the present invention.

FIG. 1 illustrates a knee orthosis 10 when worn on the right leg 11 of a patient, the orthosis including a pair of knee joint assemblies 12 and 13 positioned on opposite sides of a patient's leg with the orthotic joints or hinges 14 and 15 disposed in alignment with the knee joint of the wearer. The assemblies also include upper sidebars 12a and 13a disposed laterally and medially alongside the upper leg 11a and lower sidebars 12b and 13b extending laterally and medially along lower leg 11b. The hinges 14 and 15 have constantly changing instantaneous axes of rotation as the upper and lower sidebars are moved between extension and flexion, all as disclosed in detail in U.S. Pat. No. 4,361,142. The hinge or joint assemblies 12 and 13 are essentially the same in structure and operation as set forth in that patent except for the differences in the suspension system disclosed hereinafter. For details of the hinges, reference may therefore be had to U.S. Pat. No. 4,361,142, the disclosure which is hereby incorporated by reference.

At their upper or proximal ends, upper sidebars 12a and 13a are securely connected by rivets 16 or other suitable fastening means to a rigid or semi-rigid interfacial member or plate 17 that is shaped to conform to the contour of the anterior upper leg 11a. A suspension strap 18 formed of leather or other flexible material that is tough, durable, and substantially non-stretchable joins the ends of the arcuate interfacial member 17 and extends about the posterior of upper leg 11a. One end of the strap may be permanently secured to the interfacial member 17 (or to one of the upper sidebars 12a, 13a). The opposite end of the strap should be detachably and adjustably connected to the interfacial member 17 by Velcro patches 18a secured to the overlapping portions of the strap and interfacial member. Taken together, the interfacial member 17 and strap 18 constitute a proximal cuff that extends about the lower thigh of the wearer and immobilizes the proximal ends of the upper sidebars 12a and 13a with respect to the upper leg.

The suspension arrangement for the lower leg 11b is essentially the same as shown and described in U.S. Pat. No. 4,361,142. Specifically, the distal ends of lower sidebars 12b and 13b are connected to a rigid or semi-rigid interfacial member or plate 19 that is shaped to conform to the contour of the anterior lower leg and is secured to the distal ends of the sidebars by rivets 20 or other suitable connecting means. A suspension strap 21 similar to strap 18 extends about the posterior surface of the lower leg with one end of strap 21 being permanently secured to the interfacial member 19 and the other end being releasably connected by Velcro patches 21a or other appropriate connecting means. Interfacial member 19 and strap 20 together constitute a distal cuff that immobilizes the distal ends of lower sidebars 12b and 13b in relation to the lower leg of the wearer.

An additional cuff composed of interfacial member or plate 22 and straps 23, 24 also extends about the lower leg 11b between the wearer's knee and distal cuff 19, 21. One of the straps 23 is secured to one of the sidebars 13b by rivet 25 (or other connector); the other strap 24 is affixed by rivet 26 to the lower sidebar 12b. The ends of each strap are detachably and adjustably connected by appropriate connecting means. Vecro patches as described above and as disclosed in U.S. Pat. No. 4,361,142 may again be used. Alternatively, as shown in FIG. 1, buckles 27 (only the buckle for strap 24 is visible in that figure, although a similar buckle is provided for strap 23) may be used. If desired, one or both of the straps may extend through slots 28 in the rigid or semi-rigid interfacial member 22 to permit limited adjustment of the strap(s) in relation to that member. When the orthosis is properly fitted upon a wearer's leg, the cuff formed by interfacial member 22 and straps 23, 24 immobilizes the upper or proximal ends of the lower sidebars 12b, 13b to help prevent anterior-posterior pivotal movement of those sidebars. Thus, the distal cuff 19, 21 and the intermediate cuff 22, 23, 24 together constitute a two-point or two-zone suspension for holding the lower sidebars 12b, 13b in proper positions in relation to the patient's lower leg and to resist forces that might tend to cause undesired anterior-posterior displacement of hinges 14, 15 as well as forces tending to cause pistoning of the orthosis in its entirety.

It has found that the provision of a femoral supracondular cuff 30 is necessary to provide, along with the other cuffs, a four-point or four-zone suspension system for the knee orthosis 10. While the purpose of such a cuff is generally the same as that of cuff 22, 23, 24, namely, to restrain pivotal action of the sidebars (in this case, pivotal action of upper sidebars 12a, 13a about their proximal ends), anatomical factors tend to defeat the effectiveness of an ordinary cuff at that location. Changes in both the muscle mass and its position as the leg extends and flexes provide a moving surface about which a supracondular cuff must extend, and such movements tend to cause rather than restrain anterior-posterior pivotal movement of the lower or distal ends of upper sidebars 12a and 13a, and of the hinges 14, 15 to which they are connected, in relation to the femur 31 and femoral condyle 32 (FIG. 6). A principal change in the muscle mass involves the quadricep muscle group which changes in both size and shape in the area of the distal femoral condyle 32 just proximal to the abductor tubercle, with the muscle mass in that area enlarging as the leg extends and reducing as it flexes. Such muscle mass is indicated in outline at 33 in FIG. 6.

A supracondular cuff 30 comprises a semi-rigid but flexible member 34 of generally U-shaped configuration and flexible strap means 35 connecting the ends of the member 34 to sidebar 12a below the proximal cuff 17, 18. As shown most clearly in FIGS. 2-5, the U-shaped interfacial member 34 includes an anterior arm portion 34a a posterior arm portion 34b, and an integral intermediate or connecting portion 34c. A pivot pin 36 extends into an enlarged opening 37 in the intermediate portion 34c and the head 38 of the pin is retained within that opening by a pair of retention plates 39 and 40 secured by rivets 41 to opposite sides of the member 34. An opening 39a in plate 39 is small enough to restrain head 38 but large enough to allow limited universal swivel action of interfacial member 34 as indicated by broken lines in FIGS. 4 and 5. Specifically, the member 34 is capable of limited pivotal movement along a longitudinal transverse plane (FIG. 4) and limited movement along a sagittal plane (FIG. 5). In addition, the arm and intermediate portions of interfacial member 34 are capable of flexing to approximate the changing contour of the leg during extension and flexion.

The shank 42 of pivot pin 36 is threaded and is retained within a threaded opening 43 in the medial upper sidebar 13a. As shown in FIG. 4, the end of the shank is slotted to permit the shank to be extended or retracted axially, thereby allowing adjustment of the distance between interfacial member 34 and upper sidebar 13a. A lock nut 44 is carried by the shank and engages sidebar 13a to secure the pivot pin and the interfacial member in their selected positions of adjustment.

The pivot pin 36 should be located in close proximity to the abductor tubercle (the medial projection at the femoral condyle) and should extend transversely in a direction generally parallel with the variable and instantaneous axes of rotation of the knee. The anterior arm portion 34a arches upwardly (proximally) and laterally above patella 46 (FIG. 6) and, similarly, the posterior arm portion 34b arches upwardly (proximally) and laterally above the hamstring tendons. Strap 35 may be formed in sections with a central section 35a pivotally connected by rivet 47 (or other connecting means) to lateral upper sidebar 12a, and with a pair of outer portions 35b connected by rivets 48 to the ends of arm portions 34a and 34b (FIG. 3). Any suitable means may be provided for releasably and adjustably connecting the central and outer portions of the strap 35 together; in the illustration given, a pair of buckles 50 are provided, the central portion 35a of the strap supporting the hook elements 50a of the buckles, and the outer section 35b of the strap supporting the loop or ring portions 50b of such buckles.

A resilient pad or cushion 52 formed of foam rubber or other similar material extends over the lateral surface of the intermediate portion 34c of U-shaped member 34. The pad serves to cushion the force applied by the cuff against the abductor tubercle (the medial projection at the femoral condyle) when the leg is flexed and extended. A pad 53 may also be secured by rivet 47 to the medial side of strap 35 (and the medial side of lateral upper sidebar 12a) to enhance wearer comfort.

Strap 35 not only holds the anterior and posterior arm portions of the U-shaped member in contact with the upper leg but also limits the extent of swivel action of member 34. When the orthosis is properly fitted upon a wearer, the interfacial member 34 may swivel to a limited extent in any direction except that the non-stretchable strap 35 sets the outer limits for anterior movement of arm portion 34a and posterior movement of arm portion 34b. The result is a supracondular cuff 30 that is capable of accommodating changes in the mass and location of the upper leg muscles, particularly the muscles of the quadricep group, while at the same time stabilizing the distal ends of the upper sidebars 12a and 13a against anterior-posterior movement in relation to the femoral condyle of the knee joint. In addition, the flexible interfacial member 34 may itself alter its shape, particularly with respect to anterior-posterior flexing of the arm portions 34a and 34b, to permit such changes in muscle shape and location.

The interfacial member 34 of supracondular cuff 30 may be formed of any suitable semi-rigid material although a lightweight plastic is believed particularly desirable. Effective results have been obtained using a dense, moderately-expanded, polyvinyl chloride foam material marketed under the designation "Sintra" by Alusuisse Metals, Inc., Fair Lawn, New Jersey, but other sheet materials having similar properties may be utilized. Such foamed PVC has a foamed core but a smooth, high density outer skin, and is believed particularly advantageous because of its toughness and its capability of being reshaped when heated. Therefore, in fitting the orthosis to a patient, the supracondular cuff may be heated and its shape adjusted to conform to the contour of a wearer's leg. Such adjustment should be made with the leg extended since it is during extension that the quadricep muscles undergo greatest expansion in the supracondular region.

The supracondular cuff 30' of FIGS. 7-9 is similar to the structural already described except that the head 38' of pin 36' is disposed within a recess 55 formed within pad 52' and a helical compression spring 56 is interposed between lock nut 44' (or radial sidebar 13a) and cuff 30'. As in the previous embodiment, the maximum distance between the intermediate portion of member 34 and sidebar 13a may be adjusted by rotating the threaded shank of the pin within the threaded opening of the sidebar. However, as shown in FIG. 8, medial displacement of the cuff along the shank 42' of pin 36' may occur until spring 56 is fully compressed. Therefore, in addition to the swivel action already described in connection with cuff 30, the supracondular cuff 30' of FIGS. 7-9 is also capable of limited medial displacement and, when the forces causing such displacement are relieved, of returning into its original position under the influence of compression spring 56.

While in the foregoing we have disclosed embodiments of the invention in considerable detail for purposes of illustration, it will be understood by those skilled in the art that many of these details may be varied without departing from the spirit and scope of the invention.

We claim:

1. A knee orthosis comprising a pair of hinge assemblies adapted to be disposed on opposite sides of a wearer's knee; each hinge assembly including an upper sidebar adapted to extend upwardly alongside the wearer's upper leg and a lower sidebar adapted to extend downwardly alongside the wearer's lower leg; said hinge assembly having constantly changing instantaneous axes of rotation as said upper and lower sidebars are moved between extension and flexion; lower suspension means for securing said lower sidebars along opposite sides of a wearer's lower leg; and upper suspension means for securing said upper sidebars along opposite sides of a wearer's upper leg; said upper suspension means comprising (a) a proximal cuff connected to the proximal ends of said upper sidebars and adapted to extend about a wearer's thigh and (b) a supracondular femoral cuff connected to said upper sidebars distal to said proximal cuff; said supracondular femoral cuff including a flexible, semi-rigid member of generally U-shaped configuration having a pair of arm portions adapted to engage the anterior and posterior surfaces of the upper leg just above the knee and an integral intermediate portion disposed between said arm portions; means connecting said intermediate portion to one of said sidebars for limited universal pivotal movement in relation thereto; and flexible strap means joining the ends of said arm portions to the other of said upper sidebars.

2. The orthosis of claim 1 in which said upper sidebars comprise a medial sidebar and a lateral sidebar; said intermediate portion of said U-shaped member being pivotally connected by said means to said medial sidebar; and said strap means joining the ends of said arm portions to said lateral sidebar.

3. The orthosis of claims 1 or 2 in which said arm portions of said U-shaped member are arcuate and arch upwardly and away from said intermediate portion.

4. The orthosis of claim 3 in which said U-shaped member is formed of polyvinyl chloride sheet material having a foamed core and smooth outer skin surfaces.

5. The orthosis of claims 1 or 2 in which said means for connecting said intermediate portion of said U-shaped member to said one upper sidebar comprises an elongated pivot pin having an enlarged head and a threaded shank; said intermediate portion having an enlarged opening receiving said shank for limited universal swivel action of said member upon said pin; said head retaining said member upon said pin.

6. The orthosis of claim 5 in which said one upper sidebar is provided with a threaded opening threadedly receiving the shank of said pivot pin; said shank being rotatable in relation to said one sidebar to adjust the distance between said supracondular cuff and one sidebar.

7. The orthosis of claim 6 in which said intermediate portion of said U-shaped member is axially slidably along the shank of said pin between said head and said one sidebar; and compression spring means extending about said shank between said one sidebar and said intermediate portion for urging said U-shaped member towards said head of said pin.

8. The orthosis of claim 5 in which locking means are threadedly mounted upon said shank for engaging one sidebar for holding said shank in a selected position of adjustment.

9. The orthosis of claims 1 or 2 in which a resilient pad extends over the surface of said intermediate portion facing away from said one upper sidebar.

10. The orthosis of claims 1 or 2 in which said flexible strap means is substantially non-stretchable and detachably interconnects at least one said arm portions of U-shaped member to said other sidebar.

11. The orthosis of claim 9 in which said strap means is pivotally connected to said other sidebar for pivotal movement of said strap means in a sagittal plane.

* * * * *